United States Patent [19]
Beaver

[11] 3,969,959
[45] July 20, 1976

[54] ADJUSTING TOOL FOR SURGICAL BLADE GUARD

[76] Inventor: John R. Beaver, 21 Lincoln St., Lexington, Mass. 02173

[22] Filed: Mar. 10, 1975

[21] Appl. No.: 556,814

Related U.S. Application Data

[60] Division of Ser. No. 507,079, Sept. 18, 1974, which is a continuation of Ser. No. 332,611, Feb. 15, 1973, abandoned.

[52] U.S. Cl.................................................. 81/3 R
[51] Int. Cl.² ........................................ B25B 27/00
[58] Field of Search...................... 29/268, 283, 235; 81/5.1 R, 3 R; 30/337, 320

[56] References Cited
UNITED STATES PATENTS

| | | | |
|---|---|---|---|
| 1,179,565 | 4/1916 | Risden | 29/268 |
| 1,953,930 | 4/1934 | Dyal | 29/268 X |
| 2,700,910 | 2/1955 | Van Niel | 81/5.1 R |

*Primary Examiner*—Al Lawrence Smith
*Assistant Examiner*—J. C. Peters

[57] ABSTRACT

An adjustment tool for use with a surgical knife of the type in which a blade is provided with an adjustable guard for limiting the depth of cut. The tool has cooperating portions for engagement with the blade and the guard to permit it rapid and accurate adjustment of the position of the guard on the blade between incisions during a surgical procedure.

4 Claims, 5 Drawing Figures

U.S. Patent  July 20, 1976  3,969,959
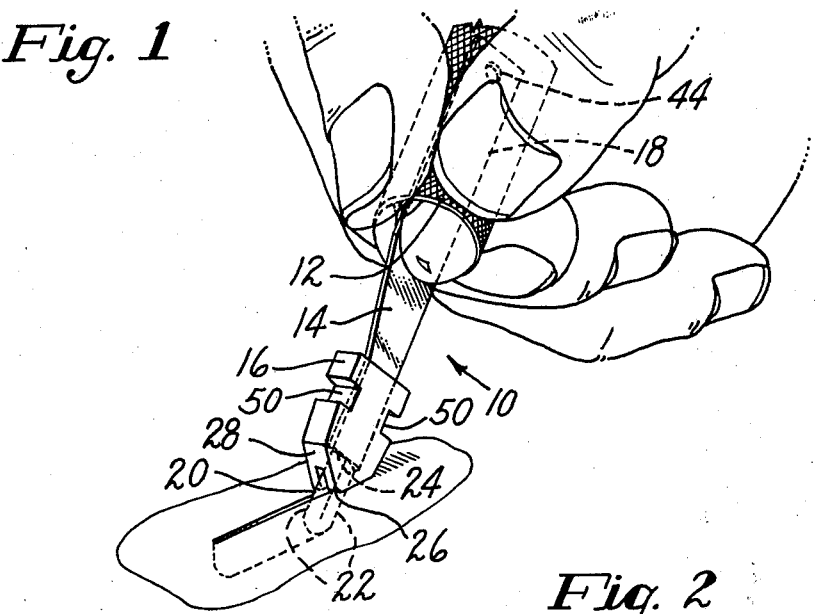
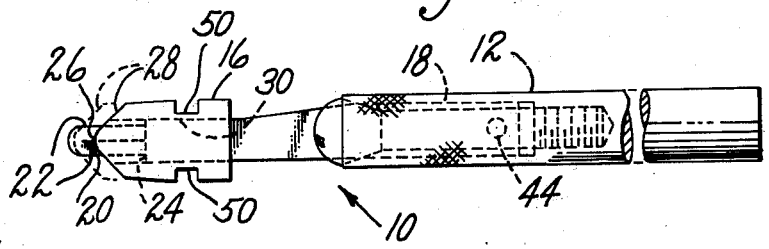
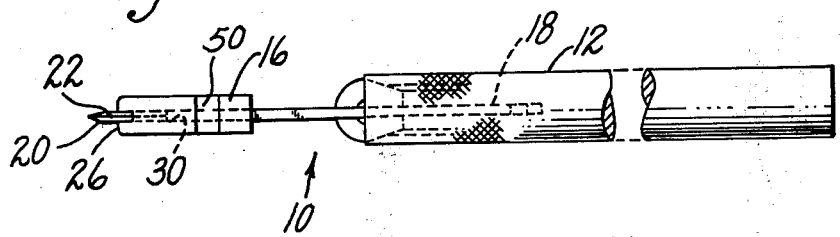
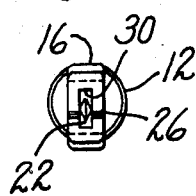
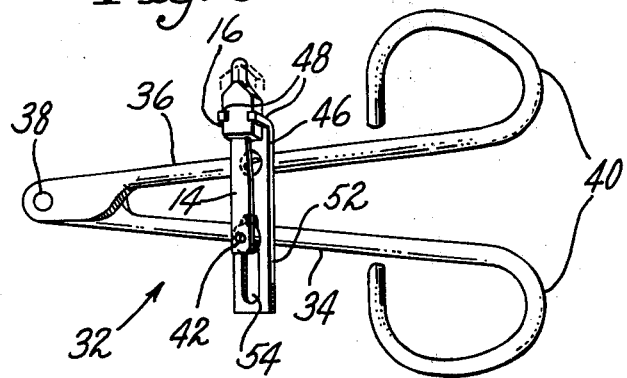

ADJUSTING TOOL FOR SURGICAL BLADE GUARD

REFERENCE TO RELATED APPLICATONS

This application is a division of my application Ser. No. 507,079 filed Sept. 18, 1974, which was a continuation of my application Ser. No. 332,611 filed Feb. 15, 1973, now abandoned.

BACKGROUND OF THE INVENTION

In many types of surgery, such as eye, vascular, plastic and neuro-surgery, accurate control of the depth of cut is of crucial importance. For example, in eye surgery, a cut only slightly deeper than intended can cause loss of eye fluid and the permanent loss of the sight of the eye. Certain types of surgery also require that a sequence of cuts be made to different depths, which depths must be accurately controlled.

BRIEF DESCRIPTION OF THE DRAWING

FIG. 1 is a perspective view of a knife embodying the features of the invention, shown in position for making an incision.

FIG. 2 is a top plan view of the knife of FIG. 1.

FIG. 3 is a view of the knife of FIG. 2 as seen from the top.

FIG. 4 is a view of FIG. 2 as seen from the left end.

FIG. 5 is a perspective view of the blade and guard portion of the knife assembled with an adjusting tool, for adjusting the position of the guard on the blade.

DESCRIPTION OF THE ILLUSTRATED EMBODIMENT

Referring to the drawing, there is illustrated a surgical knife assembly 10 with which the adjusting tool is designed for use which comprises a handle 12, a blade 14 removably assembled with the handle and a blade guard 16 assembled onto the blade.

In the illustrated embodiment the blade 14 comprises a rear tang portion 18 for assembly into the handle and a forward end 20 having cutting edges 22 formed on the outermost portion thereof. The blade 14 is formed of a flat piece of steel of uniform thickness and the cutting edges 22 are formed by grinding down the side edge portions on the forward end, so that the overall width of the sharpened portion is slightly less than the remainder of the forward end portion.

To provide adjustable means for limiting the depth of cut of the blade, the guard 16 is provided on the forward end of the blade. The guard is formed of a single piece of molded plastic such as nylon, polyethylene, or the like, and is generally rectangular in cross section with a rounded forward nose 26 and bearing surfaces 28 extending rearwardly and outwardly from the nose at an angle of about 45° to the axis of the assembled blade.

A central aperture 30 extends through the body with the dimensions thereof being such that when the guard is assembled onto the forward end of the blade, the guard frictionally grips the blade with sufficient tightness to prevent movement of the guard on the blade unless a predetermined force is applied thereto, said predetermined force being considerably greater than the force applied to the guard during any surgical cutting procedure.

In one embodiment of the invention the thickness of the blade is slightly greater than the width of the aperture 30 in the guard, so that on insertion of the blade into the guard, the flat sides of the blade cause the corresponding dimensions of the guard to become enlarged, and thereby frictionally grip the sides of the blade. In the illustrated embodiment of the invention, the aperture 30 is so dimensioned that the edges thereof either ride on or are closely adjacent the side edges of the guard.

Hence the interior surface of the guard does not touch the cutting edges 22, which might impair their cutting ability. The rear end portion 18 of the blade is wider than the portion 20, hence the guard cannot move rearwardly beyond the position at which the rear end of the guard contacts the foremost portion of the blade tang 18. The components are so dimensioned that when this occurs, almost all of the useful length of the cutting edge is exposed. A maximum depth of cut, within the capabilities of the blade, may therefore be obtained without the risk of a deeper cut that could be accidentally made if the guard were not present.

The rounded nose portion 26 and the bearing surfaces 28 of the guard extend laterally on each side of the blade to provide a broad area to bear against the surface being cut on each side of the incision and thereby prevent penetration of the blade beyond the desired depth. The surfaces 28 are inclined to the axis of the blade at an angle of about 45° since this is the maximum angle from the vertical that the knife would be held during use.

When supplied from the manufacturer the guard may be positioned on the blade so that a predetermined length of cutting edge is exposed, for use in a particular type of surgical incision. However in certain surgical procedures, a first incision may be required at one depth, and a second incision may be required shortly thereafter at a different depth.

For this reason an adjusting tool 32 is provided for use with the knife, which may have the form illustrated in FIG. 5. The tool 32 has a pair of legs 34 and 36 joined at one end at pivot 38 and having handle means 40 at the other end for grasping by the fingers. The tool 32 and the blade and guard assembly are provided with cooperating interengaging means, which, in the illustrated embodiment comprises an upstanding pin 42 on one leg 34 for entering an aperture 44 in the rear end 18 of the blade and a bracket 46 assembled onto the other leg, said bracket having a pair of upstanding legs 48 disposed thereon and spaced apart to be received in a pair of opposed notches 50 in the side edges of the guard. The position of the guard on the blade may therefore be adjusted by moving the legs 34 and 36 toward or away from each other as desired.

To limit the amount of movement applied to the guard by the tool, the bracket 46 has a portion 52 which extends over the leg 34, with an elongated aperture 54 disposed therein through which pin 42 projects. The movement of the legs in relation to each other is therefore limited by the dimensions of the aperture 54 so that the guard cannot inadvertently be completely removed from the blade, nor can the guard be forced onto the rear tang of the blade, which might enlarge the guard aperture to an undesirable degree.

Hence during a surgical procedure, after a cut of one depth is made, the blade may be removed from the handle and placed in the adjusting tool in the manner illustrated, where the guard may be adjusted to the desired position to expose the appropriate amount of cutting edge. Such adjustment can be conveniently accomplished under a pre-focused microscope with a micrometer lens, so that the amount of exposed cutting edge may be accurately determined.

Although it is, of course, possible to have on hand a number of pre-adjusted knives, the above described adjustment can be made accurately and rapidly, eliminating the possibility of accidentally picking up a knife with an improper amount of cutting edge exposed.

In the illustrated embodiment the guard is designed to frictionally grip the side edges of the blade, however it will be understood that the blade may have other shapes and the guard may be designed to frictionally grip other portions of the blade.

Since certain other obvious changes may be made in the illustrated embodiment of the invention, it is intended that all matter contained herein be interpreted in an illustrative and not a limiting sense.

I claim:

1. A tool for receiving an elongated blade having a movable guard frictionally positioned thereon to adjust the position of the guard on the blade, comprising a pair of members pivoted at one end so as to be movable in a plane towad and away from each other and having handles at the other end, and means projecting from the members between the pivot and the handles in a direction perpendicular to the plane of movement for supporting and engaging the blade and guard assembly to cause relative motion therebetween with relative motion between the handles.

2. A tool for receiving an assembly comprising a blade and blade guard for adjusting the position of the blade guard on the blade, comprising a pair of members joined at a pivot and having handles at one end, a bracket overlying the members, said bracket being attached to one of said members and having a slot in the portion overlying the other member, said bracket having means at one end for engaging one component of said assembly, said other member having means extending therefrom through the slot in said bracket for engaging the other component of the assembly.

3. A tool as set out in claim 2 in which the bracket is disposed between the pivot and the handles.

4. A tool for receiving an assembly comprising a blade and blade guard for adjusting the position of the blade guard on the blade, comprising a pair of members joined at a pivot and having handles at one end, a bracket extending between the members, said bracket being secured to the members so as to be pivoted to one member and slidable transversely in relation to the other member, said bracket having means thereon for engaging one component of the assembly and said other member having means for engaging the other component of the assembly.

* * * * *